United States Patent [19]

Demers et al.

[11] 4,300,834
[45] Nov. 17, 1981

[54] INDUCTIVELY COUPLED PLASMA ATOMIC FLUORESCENCE SPECTROMETER

[75] Inventors: Donald R. Demers, Nashua, N.H.; Charley D. Allemand, Newton, Mass.

[73] Assignee: Baird Corporation, Bedford, Mass.

[21] Appl. No.: 152,387

[22] Filed: May 22, 1980

[51] Int. Cl.³ .................... G01N 21/64; G01N 21/73
[52] U.S. Cl. ................................. 356/316; 356/315; 356/317; 356/417; 313/209
[58] Field of Search ............................. 356/311–318, 356/417; 250/461 R, 461 B

[56] References Cited

U.S. PATENT DOCUMENTS

| | | | |
|---|---|---|---|
| 2,847,899 | 8/1958 | Walsh. | |
| 3,428,401 | 2/1969 | Buzza | 356/187 |
| 3,619,061 | 11/1971 | Mitchell | 356/85 |
| 3,958,883 | 5/1976 | Turner | 356/85 |

FOREIGN PATENT DOCUMENTS 46-12432 3/1971 Japan .................... 356/315

OTHER PUBLICATIONS

Measures et al. "Analyzing Fluorescence Decay". *Laser Focus*, Nov. 1974, pp. 49–52.
Mitchell et al. "Simultaneous Multielement Analysis Using Sequentially Excited Atomic Fluorescence Radiation", *Spectrochimica Acta*, vol. 25B, No. 4, pp.175–182.
D. G. Mitchell & A. Johansson, title unknown, 5 *Spectrochimia Acta* 1971, pp. 178–180.
V. A. Fassel & R. N. Kniseley, "Inductively Coupled Plasma-Optical Emission Spectroscopy", *Analytical Chemistry*, vol. 46, No. 13, Nov. 1974, pp. 1110A-1120A.
V. A. Fassel & R. N. Kniseley, "Inductively Coupled Plasma,"*Analytical Chemistry*, vol. 46, No. 13, Nov. 1974, pp. 1155A–1164A.
A. Montaser & V. A. Fassel "Inductively Coupled Plasma as Atomization Cells . . . ", *Analytical Chemistry*, vol. 48, No. 11, Sep. 1976, pp. 1490–1499.
V. A. Fassel, "Quantitative Elemental Analyses by Plasma Emission Spectroscopy,"*Science*, vol. 202, 13 Oct. 1978, pp. 183–191.

*Primary Examiner*—F. L. Evans
*Attorney, Agent, or Firm*—Morse, Altman, Oates & Dacey

[57] ABSTRACT

An inductively coupled plasma atomic fluorescence spectrometer (ICP-AFS) for multielement analysis of unknown samples. The ICP-AFS spectrometer comprises a plasma stream atomizing a dispersed sample and directed along a central axis, a plurality of optical stations surrounding the central axis, each including an energizing illuminator and a fluorescence detector focused at the same region of the plasma stream, and a readout system for identifying the unknown samples. Preferably, the plasma stream is controlled by inductive coupling, the energizing illuminator is a modified hollow cathode lamp, the fluorescence detector includes an interference filter, and the readout system incorporates multiplexing and intermittent modulation of the energizing illuminators.

11 Claims, 8 Drawing Figures

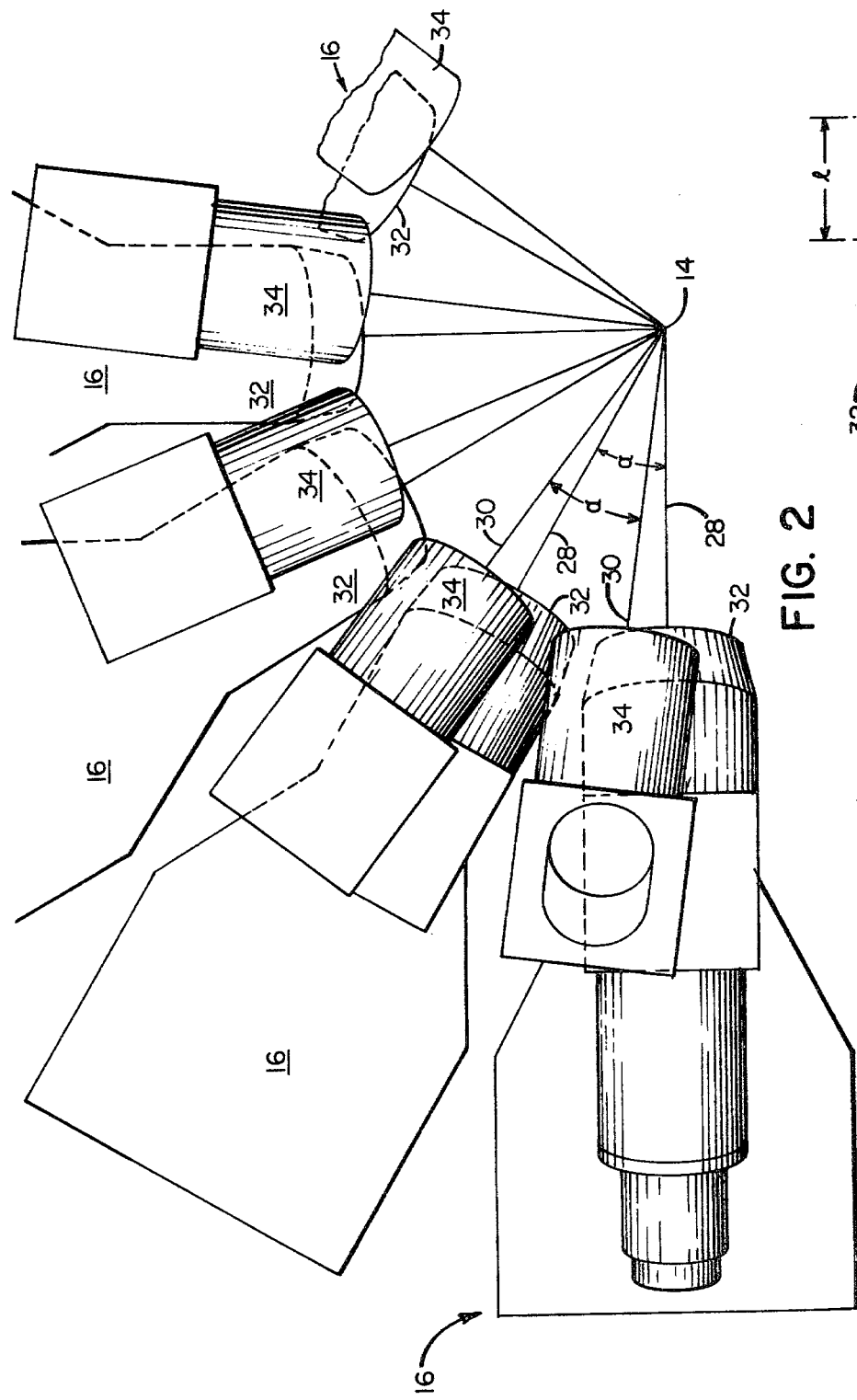
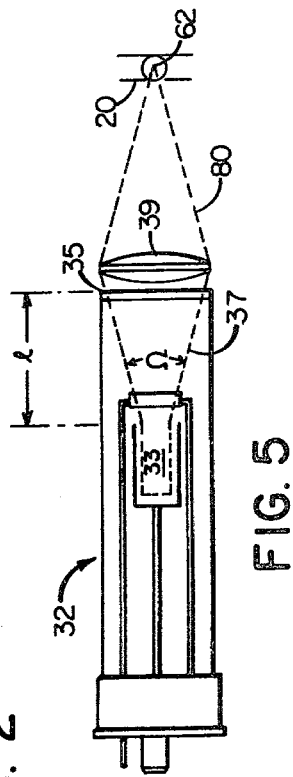

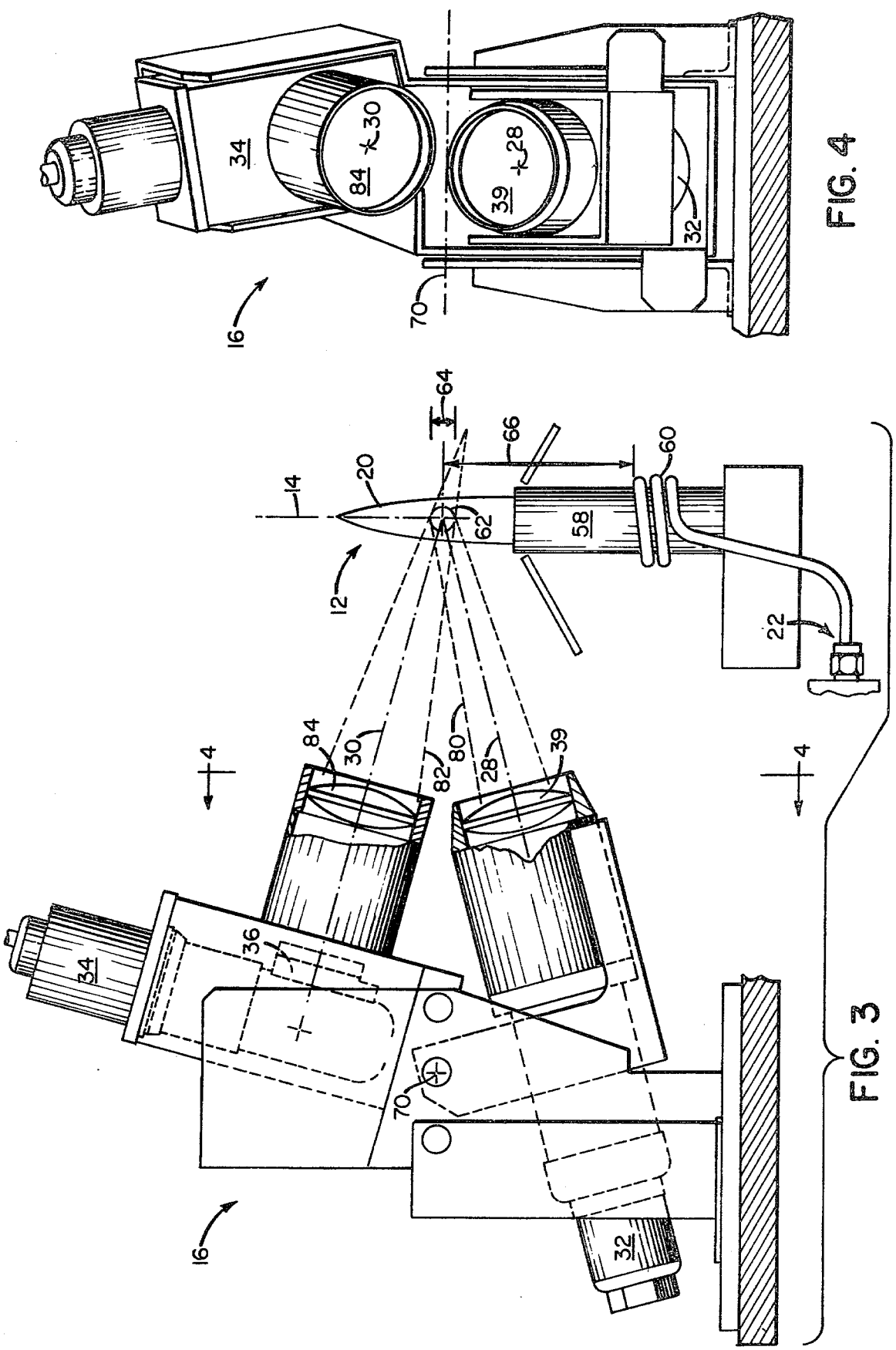

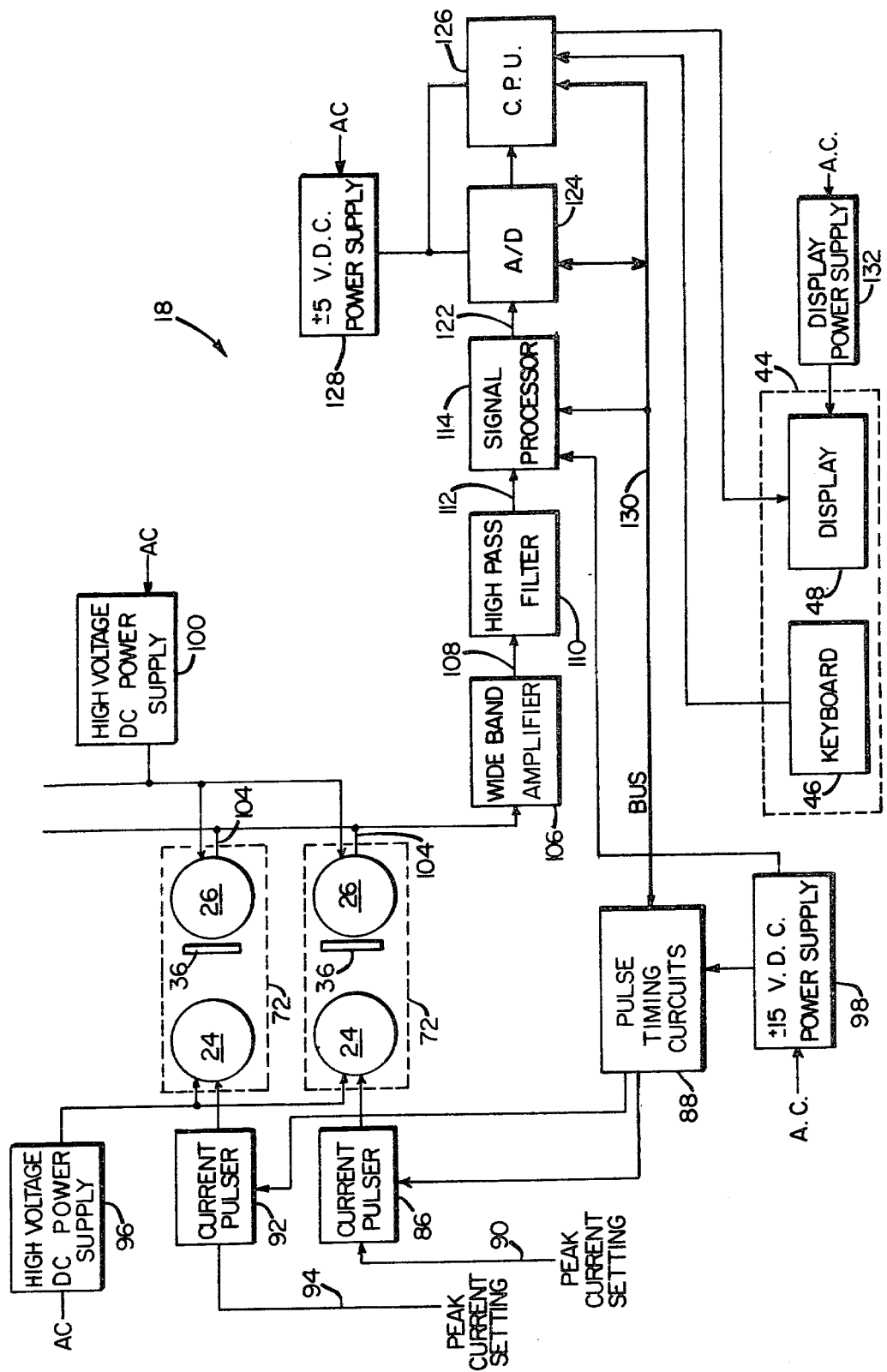

INDUCTIVELY COUPLED PLASMA ATOMIC FLUORESCENCE SPECTROMETER

BACKGROUND OF THE INVENTION

1. Field of the Invention

The present invention relates generally to fluorescence spectrometers and, more particularly, to the spectroscopic analysis of unknown samples by an inductively coupled plasma atomic fluorescence spectrometer.

2. The Prior Art

Until the early 1960's, general purpose atomic spectroscopy measurements had been carried out by using flame atomic emission (FAE) instruments. FAE instruments employ no external excitation source. Rather, in FAE instruments the free atoms are excited by thermal collision with high energy species of the atomization source (e.g., the flame gas atoms), and a portion of the excited atoms undergoing radiational deactivation is measured. In atomic emission (AE) spectroscopy, all of the possible energy levels above the ground state of a given element are populated and all of these excited levels are undergoing radiational deactivation. Consequently, AE spectra are spectral-line rich, particularly where the sample analyzed contains more than one element.

In the 1960's, flame atomic absorption spectroscopy (FAAS) instruments came increasingly into use. These FAAS instruments employ a separate excitation source, such as a hollow cathode lamp, for each element being analyzed in a sample, in addition to the flame and the monochromator used in an FAE instrument. In flame atomic absorption (AA) spectroscopy, the atomization source (i.e., the flame) functions primarily to dissociate a sample into its constituent atoms and to leave the latter in their lowest energy state, i.e., the ground state of energy level. It is the function of the separate excitation source in AA spectroscopy to excite some of these free atoms in the ground state to a higher state of energy level. In so doing, these atoms absorb some of the excitation source radiation, and the fraction absorbed, relative to when there are no atoms of the element analyzed for present in the atomization source, is indicative of the concentration of that element in the sample. In an AA instrument, the resultant spectra are unambiguous and simple since each element absorbs best at its characteristic wavelength. The signal observed at this characteristic wavelength is indicative of the concentration of that element in the sample. In an AA instrument, however, the radiation from the separate excitation source, the atomization source and the detector are all required to be mounted along the same axis. Because of this constraint, it is extremely difficult to design any multichannel AA instrument for multielement analysis. Consequently, multielement AA analyses are carried out sequentially on single channel AA instruments.

No such constraint exists in atomic fluorescence (AF) spectroscopy. In contrast to AA spectroscopy, in AF spectroscopy the excitation source can be mounted anywhere off the atomization source-detector axis. Most AF spectroscopic instruments arrange the excitation source and the detector at right angles to each other and in a horizontal plane when viewing the isotropically emitted fluorescence radiation from the analyte in the atomization source. Consequently, designing a multichannel AF instrument for multielement analysis is inherently simpler that with AA. Furthermore, it is a characteristic of AF that the AF spectra are simple, as in AA.

During the 1970's, a promising new atomization source emerged—the inductively coupled plasma (ICP). A plasma is defined as a luminous gas, a significant fraction of whose atoms or molecules is ionized. Plasmas therefore are considered to be gaseous conductors. As such, plasmas readily interact with magnetic fields, making it possible to couple a plasma to a high frequency power source. The emergence of the inductively coupled plasma (ICP) led to the widespread use of ICP—Atomic Emission Spectroscopy (AES) systems, particularly, in the simultaneous multielement analysis (SMA) for many trace elements. For unlike in AA and in AF spectroscopy, in an ICP-AES system, no separate excitation source for each element being analyzed is required. Consequently, SMA can be done in a relatively simple manner.

An ICP-AES system, however, suffers from a serious disadvantage and that is the problem of spectral line interference. This problem of spectral line interference is particularly severe when analyzing a sample for traces of metals in the presence of other metals such as tungsten, cerium, uranium, iron, vanadium and the like. It has been found that these and many of the transition series metals as well as all of the lanthanide series metals are spectral-line rich in the 220–420 nm wavelength region commonly employed in a typical ICP-AES analysis. As a consequence, any ICP-AES system must include a high resolution spectrometer. Nonetheless, an ICP-AES analysis of a sample containing a number of metals at concentrations above their respective detection levels still exhibits numerous instances of overlap of the emission lines of the elements present in the sample. The analyst then has to unravel which fraction, if any, of the total measured atomic emission signal in each channel is from an intended element and which fraction (or fractions) is (or are) from an interfering element (or elements). Slit changes and the use of computers to help disentangle the overlay are required to produce reliable and accurate results. Furthermore, the bandwidth of the atomic emission line in the wings in ICPs (and also in flames) can be 0.5 Angstroms or more. Thus, the designing of a spectrometer with a resolution better than 0.5 Angstroms, while reducing the number of instances of spectral line overlap interferences, would still not eliminate them. The problem of spectral line overlap interference, therefore, is and remains a fundamental limitation to the employment of ICP-AES systems.

SUMMARY OF THE INVENTION

It is a principal object of the present invention to overcome the above disadvantages by providing an inductively coupled plasma atomic fluorescence spectrometer (ICP-AFS) system for the simultaneous multielement analysis (SMA) of unknown samples.

More specifically, it is an object of the present invention to provide an ICP-AFS system comprising an inductively coupled plasma for atomizing a dispersed sample directed along its central axis, a plurality of optical stations radially disposed about the central axis, each station including an energizing illuminator and a fluorescence detector directed at the same region of the plasma stream, and a readout system coupled to the optical stations for identifying the unknown samples. Preferably, the energizing illuminator is a modified hollow cathode lamp characterized by collectibility of a wide angle of high intensity radiation, the fluorescence detector includes an optical interference filter matched to the characteristic radiation of the energizing illuminator, and the readout system incorporates multiplexing and intermittent modulation of the energizing illuminators.

Other objects of the present invention will in part be obvious and will in part appear hereinafter.

The invention accordingly comprises the ICP-AFS system of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 2 is a plan view, on an enlarged scale, of a portion of the ICP-AFS instrument shown in FIG. 1;

FIG. 3 is a front elevation of a part of the ICP-AFS instrument portion of FIG. 2;

FIG. 4 is a side elevation, in the direction of the arrows 4—4 of FIG. 3, of the instrument part shown in FIG. 3;

FIG. 5 is a schematic view of a hollow cathode lamp modified in accordance with the invention;

FIG. 6 is a block diagram of a readout system, incorporating multiplexing and intermittent modulation, for the ICP-AFS instrument shown in FIG. 1;

DETAILED DESCRIPTION OF THE PREFERRED EMBODIMENT

Figure 1:
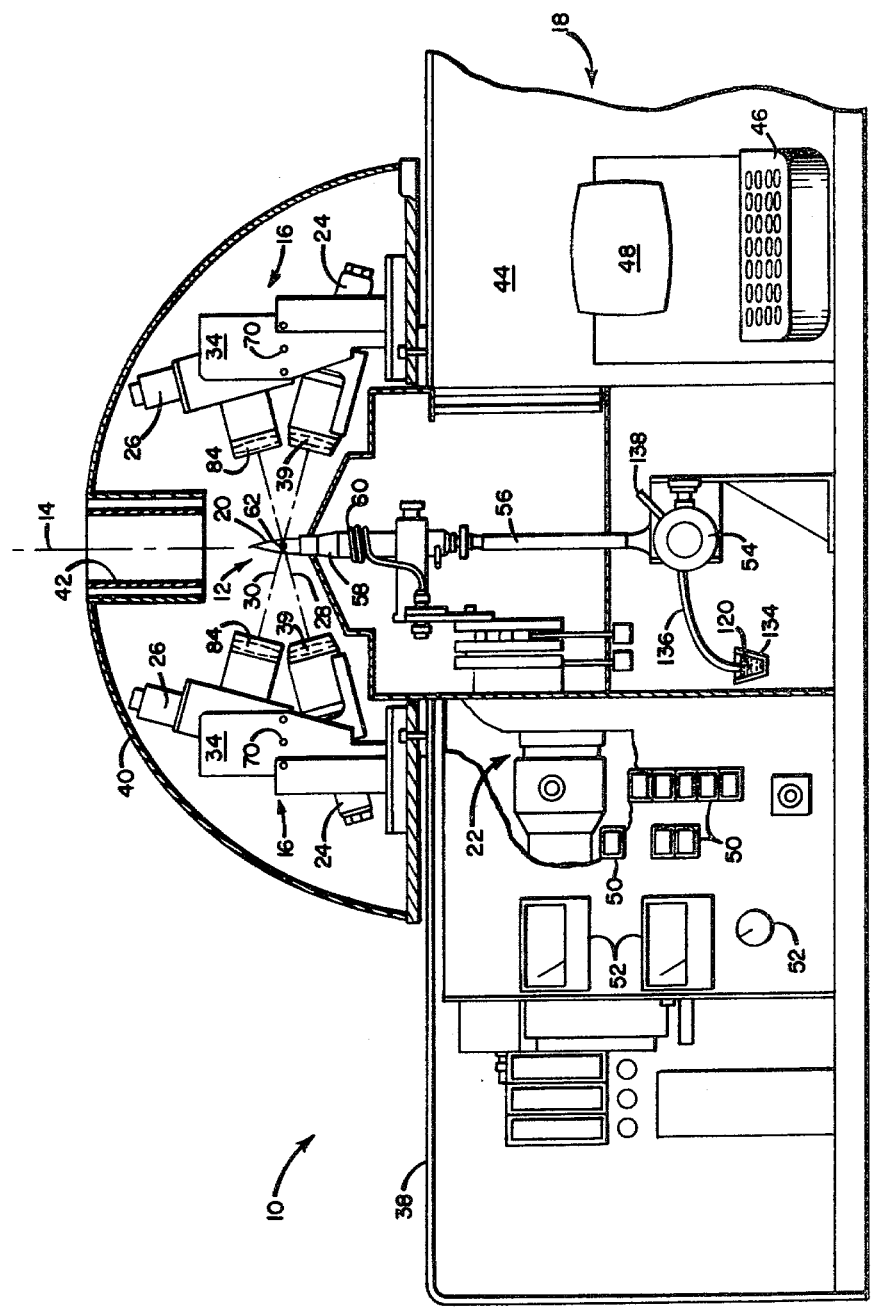
FIG. 1 is a front elevational section, with parts broken away, of an ICP-AFS instrument constructed in accordance with the present invention.

Generally, the illustrated embodiment of an inductively coupled plasma atomic fluorescence spectrometer (ICP-AFS) instrument 10 for the simultaneous multielement analysis (SMA) of unknown samples in solution comprises an atomization source 12 directed along a central axis 14, a plurality of optical stations 16 radially disposed about the central axis 14, and a readout system 18 for identifying the unknown samples. Preferably, the atomization source 12 is a plasma stream 20 controlled by inductive coupling to a radio frequency (rf) generator 22 of the type shown in U.S. Pat. No. 3,958,883 granted May 25, 1976 to Arthur S. Turner and assigned to the assignee of the present application. The teachings of this U.S. Pat. No. 3,958,883 regarding radio frequency generators are incorporated herein by reference. Alternatively, the atomization source 12 can be a flame, an electrothermal atomizer or other type of plasma not necessarily controlled by radio frequency. Each of the plurality of optical stations 16 includes an energizing illuminator 24 and a fluorescence detector 26 directed along axes 28 and 30, respectively and pointed at the same region in the plasma stream 20. Preferably, the energizing illuminator 24 is a hollow cathode lamp 32 (note FIG. 5) modified in accordance with the invention so that a wide angle of high intensity radiation is collected from the cathode. Also preferably, the fluorescence detector 26 is a photomultiplier tube 34 that includes an optical interference filter 36 matched to the characteristic radiation of its associated hollow cathode lamp 32, observe FIG. 3. Further preferably, the readout system 18 incorporates multiplexing and intermittent modulation of the energizing illuminators 24, as will be more fully described below with reference to FIG. 6.

As shown in FIG. 1, the ICP-AFS instrument 10 is a bench-type instrument that includes a base cabinet 38 mounting a central cover 40 provided with an exhaust chimney 42. The base cabinet 38 houses, behind a front panel 44, the readout system 18 and the radio frequency generator 22. The readout system 18 includes a keyboard 46 and a display 48 mounted on the front panel 44. The front panel 44 also accommodates a plurality of control buttons 50 and a number of gauges 52 that are required for the operation of the ICP-AFS instrument 10. A sample nebulizer 54 is mounted in the central portion of the base cabinet 38, and communicates via a tube 56 with a plamsa torch 58. An induction coil 60 surrounds the plasma torch 58 and connects to the rf generator 22 to deliver, by inductive coupling, a tuned and matched rf power to the plasma stream 20. The function of the plasma stream 20 in the ICP-AFS instrument 10 is simply to atomize the sample, producing a large ground state population thereof. It is not a function of the plasma stream 20 also to excite this ground state population to higher energy levels, as is the case in an ICP-AFS instrument. Consequently, the plasma stream 20 is operated at a forward rf power well above that needed to maintain a stable plasma discharge but considerably lower than that used for ICP-AES. Further, and as may be best observed in FIG. 3, the hollow cathode lamp 32 and the photomultiplier (PM) tube 34 are each directed at a region 62 of the plasma stream 20, which is not only common to both but is also somewhat higher in the plasma stream 20 than is the case in an ICP-AES instrument. The region 62 is characterized by being about six mm in diameter, as indicated by the size of arrow 64, and whose center is about fifty-five to about seventy mm above the top turn of the induction coil 60, as indicated by the size of arrow 66. It is important to keep disturbances at a minimum in the region 62 of the plasma stream 20 being viewed by one or more of the optical stations 16. Since this region 62 is located relatively high in the stream 20, the outer tube of the plasma torch 58 has been extended somewhat above the induction coil 60, as indicated by the size of arrow 68, defining a length of about forty mm. This extended plasma torch 58 prevents air entrainment to and consequent flickering of the plasma stream 20. Due to the combined effects of operating the plasma stream 20 at a lower forward rf power and of observing higher up in the plasma stream 20, the atomization source 12 background signal ($I_b$) has been considerably reduced. This lower background signal ($I_b$), in turn, results in an improved signal to noise (S/N) ratio for the ICP-AFS instrument 10. Other and further factors bearing on improving the S/N in the instrument 10 will be indicated below. It is pointed out that the region 62 of the plasma stream 20 being observed by one or more of the optical stations 16 can be adjusted independently for each station 16 up or down about a pivot axis 70, further to optimize conditions. It is also noted that these optical stations 16 are replaceably mounted to facilitate servicing of the optical stations 16. Replaceability also permits rapid changeover to another mixture of optical stations 16.

Figure 7:
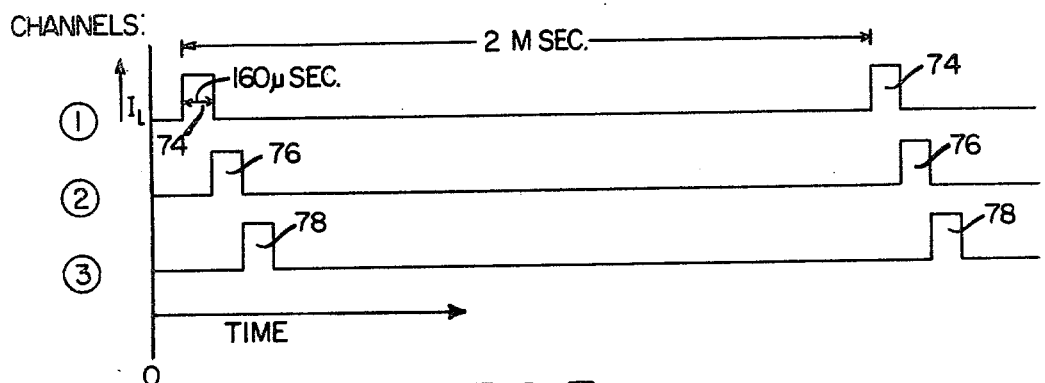
FIG. 7 depicts trains of pulses for the intermittent modulation of three channels of the ICP-AFS instrument of FIG. 1.

An observation of FIGS. 2-4 discloses that each of the plurality of optical stations 16 is radially disposed about the central axis 14 in a piggyback array, with the respective hollow cathode lamps 32 and PM tubes 34 superimposed, but not in the same vertical plane. The lamps 32 and the tubes 34 are vertically offset from each other to reduce the detection of reflected light from surfaces of objects within the cover 40 to insignificant levels. This construction permits quite a number, twelve, as herein illustrated of optical stations 16 to be mounted in one ICP-AFS instrument 10. The stations 16 are separated by an angle ($\alpha$) of 30°. Each of these optical stations 16 represents a separate channel 72 (note FIG. 6), one for each element being measured in a sample. The respective hollow cathode lamp 32 of each channel 72 is designed to emit a characteristic radiation to serve as an excitation source for a particular element. Likewise, its respective PM tube 34 of each channel 72 is provided with an optical interference filter 36 that is matched to the characteristic radiation of its associated hollow cathode lamp 32. For reasons more fully described below, the hollow cathode lamps 32 of each channel 72 are intermittently modulated by respective trains of pulses 74, 76 and 78, as depicted in FIG. 7. The temporal sequencing of the pulse trains 74, 76 and 78 is maintained during sample measurements only. Shortly (i.e., about ten seconds) after the completion of a sample measurement, all pulsing of the energizing illuminators terminates and remains terminated until another sample measurement is called for. Using this intermittent mode of pulsing, it is found that the output intensity of the energizing illuminators is constant with time, much more so than with continuous modulation. Consequently, the net fluorescence signal intensities are very stable with time, the interval between instrument restandardization can be increased, and the useful life of the energizing illuminators is increased.

Furthermore, each of the hollow cathode lamps 32 is modified as shown in FIG. 5. This modification essentially includes decreasing the distances (1) that normally separates the hollow cathode 33 from its front window 35. In a conventional hollow cathode lamp, this distance (1) is typically seventy to ninety mm. In the modified hollow cathode lamp 32 of the invention, this distance (1) has been reduced to no more than fifty mm, and preferably to about forty mm. This modified construction permits closer positioning of an optical collecting element 39 to the cathode 33, and, in turn, a larger fraction, i.e., a wider angle 37 ($\Omega$) of the high intensity excitation radiation emitted from the hollow cathode 33 can be collected and focused, as at 80, onto the viewing region 62 of the plasma s-ream 20 than has been hitherto possible. This larger cone 37 of high intensity of excitation radiation is, in turn, also responsible for further improving the S/N ratio of the ICP-AFS instrument 10.

As already mentioned, the directed characteristic excitation radiation 80, emanating from the modified hollow cathode lamp 32 and striking the region 62 of the plasma stream 20, is absorbed by the free atoms of the particular element under investigation in their lowest energy state, e.g., the ground state. The radiationally excited free atoms of the particular element in the plasma stream 20 due to this absorption are moved up from the ground state of energy level to a first excited state of energy level. Immediately after this radiational excitation of the free atoms due to absorption, the excited free atoms re-emit their absorbed energy by emitting a photon, usually of the same energy as that absorbed, i.e., the phenomenon known as atomic fluorescence. There is also some thermally excited emission occurring from the free atoms in the plasma stream 20 at the same time. In FIG. 3, a solid angle of fluorescence radiation 82, and including some thermally excited emission, is shown emanating from the region 62 of the plasma stream 20. This solid angle of fluorescence radiation 82 is next focused by a focusing lens 84 onto the optical interference filter 36 of the PM tube 34. The particular PM tube 34 detects the radiation 82 from the radiationally excited free atoms, the radiation from the thermally excited free atoms, and the radiation from the atomization source background. In order to reduce the signal intensity of the latter, and its attendant noise, the optical interference filter 36 is matched to the characteristic wavelength of the focused excitation radiation 80. Noise contributions from other wavelength regions of the plasma are thus excluded. Spectral separation of the remaining component fractions of the radiation 82 (the radiationally excited free atoms, i.e., atomic fluorescence, and the thermally excited free atoms, i.e., atomic emission) does not occur as both fractions passing through the optical interference filter 36 are at the same wavelength. These two component fractions of the radiation 82 are, however, effectively separated by the readout system 18 hereafter to be described. The illustrated PM tube 34 shown in FIG. 3 is of the side-on type. However, either a side-on type or an end-on type PM tube can be used in the ICP-AFS instrument 10.

Figure 8:
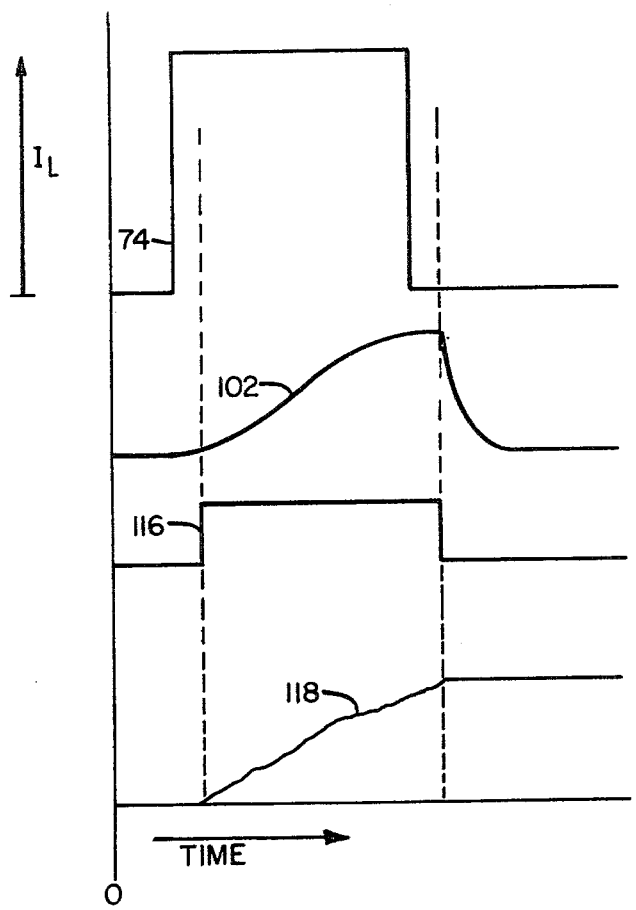
FIG. 8 depicts signal processing of one channel in the readout system of FIG. 6.

A block diagram of the preferred readout system 18 for the ICP-AFS instrument 10 is disclosed in FIG. 6. As mentioned, the readout system 18 incorporates time division multiplexing of the energizing illuminators 24 so as to achieve a temporal separation of the fluorescence radiation signals 82 from each optical station 16 and modulation of the energizing illuminators 24 to make possible the separation of the fluorescence radiation from the thermally excited emission radiation. FIG. 7 depicts trains of current pulses 74, 76 and 78 for the first three channels 72 in the readout system 18 of the ICF-AFS instrument 10. FIG. 8 on the other hand, depicts a preferred form of synchronous signal processing for but one channel 72 in the readout system 18.

The train of rectangular current pulses 74 for the first channel 72 in the readout system 18 is generated by a current pulser 86 under the control of pulse timing circuits 88. The height ($I_L$) of the rectangular current pulses 74 is determined by a peak current setting 90, and the pulses' 74 duration (160 $\mu$sec) and the time interval (2 m sec) between the pulses 74 are determined by one of the pulse timing circuits 88. The duration (160 $\mu$sec) of the current pulses 74 represents the time during which the energizing illuminator 24 is "on", and the time interval (2 m sec) between the pulses 74 represents the time during which the energizing illuminator 24 is "off". This pulsed multiplexed operation of the energizing illuminators 24 produces a greater than linear increase in radiation intensity from the illuminators 24 and minimizes noise from the atomization source 12 because only noise present during the "on" time of the illuminators 24 is measured. That is, large gains in signal to noise ratio result from pulsed operation. In addition, fluorescence signals from different analyte species are temporally separated, and life of the energizing illuminators 24 is maintained. As already stated, pulsed multiplex operation occurs only during a sample measurement. Between sample measurements, the energizing illuminators 24 are off.

Each channel 72 has its own current pulser and its own pulse timing circuit. Thus, the train of rectangular current pulses 76 for the second channel 72 is generated by a current pulser 92, having its own peak current setting 94. The duration (160 $\mu$sec) of the pulses 76 and the time interval (2 m sec) between the pulses 76 are determined by another of the pulse timing circuits 88.

Operating power for the energizing illuminators 24 is provided by a high voltage (500 V) direct current power supply 96. Operating power for the pulse timing circuits 88, on the other hand, is provided by a low voltage ($\pm 15$ V) direct current power supply 98. Both high and low V.D.C. power supplies 96 and 98 derive their respective power from a conventional A.C. power source (indicated simply A.C. in FIG. 6), be it a 120 V.A.C. or a 240 V.A.C. source, and be it a 50 Hz or a 60 Hz source. Operating power for the fluorescence detectors 26 is provided by another high voltage (1,000 V) direct current power supply 100.

As already mentioned, in FIG. 8 there is shown the signal processing of one channel 72 in the readout system 18 of the ICP-ASF instrument 10. A square wave current pulse ($I_L$) 74 of predetermined duration (preferably about 160 $\mu$sec) is applied to the energizing illuminator 24. The application of the pulse ($I_L$) 74 causes the energizing illuminator 24 to emit its characteristic radiation as a light output 102. Light output 102 is not instantaneous with the applied pulse 74 but is somewhat delayed therefrom. Light output 102 is also not a square wave. The output current signal of the fluorescence detector 26 appearing at its output line 104 however, follows exactly the light output 102 of the energizing illuminator 24 in timing, shape and duration. This output current signal of the fluorescence detector 26 includes both an a.c. component, representative of the fluorescence radiation 82 passed by the optical interference filter 36, and a d.c. component, representative of thermal emission occurring at the same wavelength and of ICP background emission. This output current signal appearing on output line 104 is coupled to a wide band amplifier 106 and is converted thereby to a representative amplified voltage. The representative amplified voltage at the output 108 of the wide band amplifier is coupled to a high pass filter 110. The high pass filter 110 removes the low frequency a.c. and d.c. noise components that are present on the higher frequency a.c. fluorescence signal. The output 112 of the high pass filter 110 is coupled to a signal processor 114, also powered by the $\pm 15$ V.D.C. power supply 98. The signal processor 114 is essentially a three-mode integrator including an electronic gate. The three-modes include an integrate mode, a hold mode and a dump (reset) mode. An electronic gate pulse 116, slightly displaced when compared to the applied pulse 74 so as to maximize the S/N ratio, and applied in the signal processor 114, insures that integration, as represented by an analog integrate signal 118, in the integrate mode occurs only for the duration of the pulse 74. During the time intervals between the current pulses ($I_L$) 74 (preferably about 2 m sec between two pulses 74), the three-mode integrator of the signal processor 114 operates in the hold mode, and continues cumulative integration, as at 118, during the pulses 74.

During the measurement of a sample solution, at least five and not more than five hundred current pulses 74 are accumulated per each channel 72 on the three-mode integrator. Once all fluorescence radiation measurements of the sample solution 120 in each of the selected channels 72 have been integrated in the signal processor 114, its output 122 is once again held in the hold mode until the output 122 is sampled by an A/D converter 124. The A/D converter 124 converts the cumulative analog integrate signal 118 to digital form suitable for digital storage and for further digital signal processing by a C.P.U. 126. Following the signal sampling by the A/D converter 124, the three-mode integrator in the signal processor 114 is switched into the dump mode, resetting thereby the integrator to zero in preparation for the next measurement of a further sample solution. In cases where the signal level is large and the integrator reaches a large voltage before the end of an individual sample measurement cycle, the A/D converter 124 samples the integrator, the integrator is then switched into the dump mode and reset to zero (these steps occur during the "off" time of the channel 72), and the integrator begins accumulating anew. In this manner, a large dynamic range of signals can be accommodated.

Operating power for the C.P.U. 126 and the A/D converter 124 is provided by a $\pm 5$ V.D.C. power supply 128. The signal processor 114, the A/D converter 124 and the pulse timing circuits are each under the control of the C.P.U. 126 and are connected to each other via a bus line 130. Input to the C.P.U. 126 is effected through the keyboard 46 and the results of the fluorescence measurements are visually displayed at the display 48, both located at the front panel 44 of the ICP-AFS instrument 10. Operating power for the display 48 is provided by a display power supply 132. The sample solution 120, contained in a sample cup 134, is presented to an aspirator nozzle 136 which is connected to the nebulizer 54. It is pointed out the ICP-AFS instrument 10 can be equally well operated in conjunction with an automatic sampler (not shown) designed to present sample solutions from a plurality of sample containers arranged on the automatic sampler, as known.

Since the atomization source 12, i.e., the ICP, in the ICP-AFS instrument 10 is operated with a forward rf power which is less than normally used in an ICP-AES instrument, the temperatures reached by the analyte species are also lower than in ICP-AES, and it has been found that some of the refractory elements present in the sample solution 120 are not efficiently dissociated into atoms. Rather, some of these refractory elements, such as aluminum, titanium, vanadium, tungsten, boron, etc., remain present as principally oxides of these elements in the plasma stream 20. Consequently, the atomic fluorescence signals 82 from this class of elements are weak or undetectable. In order to render the ICP-AFS instrument 10 amenable also to measure these refractory metals with good sensitivity, a suitable reducing agent, one containing carbon, is added in very small amounts via a separate entry port 138 into the sample nebulizer 54, observe FIG. 1. Reducing agents found suitable include the propane and methane gases and ascorbic acid (the latter being added as an aliquot to the liquid sample solution 120). The admixture of such a reducing agent with the sample solution 120 in the nebulizer 54 results, it is believed, in the following chemical equilibrium shift in the plasma stream 20: $MO + C \rightarrow M + CO_2$ where MO is the metal oxide, C is carbon and M is the free metal. The carbon of the added reagent reduces the metal oxide to the free metal which can then be excited to atomic fluorescence detectors 26 of the ICP-AFS instrument 10. The adding of the reducing agent can also take place via the sample solution 120 itself, the plasma torch 58, the nebulizer aspirator chamber, or at other places along the sample introduction system.

Thus it has been shown and described an ICP-AFS instrument 10 designed for the multielement analysis of unknown samples, which instrument 10 satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A fluorescence spectrometer for multielement analysis of samples comprising:
   (a) a source for atomizing a dispersed sample directed along a central axis;
   (b) a plurality of energizing illuminators radially mounted about said source for irradiating said atomized sample in said source;
   (c) a plurality of fluorescence detectors also radially mounted about said source for detecting fluorescent emission from said irradiated atomized sample in said source;
   (d) said illuminators and said detectors arranged in pairs, with each of said pairs viewing a region of said source common to one specific illuminator and one specific detector, each of said detectors including means matched to the characteristic radiation of said corresponding illuminator in said pair, with the height of said common region in said source being adjustable along the axial length of said source for each said pair of illuminators and detectors; and
   (e) a readout system coupled to said plurality of detectors including a multiplexer and means for intermittent modulation of said energizing illuminators.

2. The fluorescence spectrometer of claim 1 wherein said atomization source is a plasma stream.

3. The fluorescence spectrometer of claim 2 wherein said plasma stream is controlled by an inductively coupled radio frequency generator.

4. The fluorescence spectrometer of claim 1 wherein said atomization source is a flame.

5. The fluorescence spectrometer of claim 1 wherein said atomization source is an electro-thermal atomizer.

6. The fluorescence spectrometer of claim 1 wherein said energizing illuminator is a modified hollow cathode lamp characterized by a construction enabling the collection of a wide angle of radiation from its hollow cathode.

7. A fluorescence spectrometer for multielement analysis of samples comprising:
   (a) a plasma stream for atomizing a dispersed sample and directed along a central axis;
   (b) an rf generator inductively coupled to said plasma stream for delivering a tuned and matched rf power to said plasma stream, said rf generator being operated at a low forward rf power sufficient to maintain a stable plasma stream;
   (c) a plurality of optical stations radially disposed about said central axis, each of said optical stations including an energizing illuminator and a fluorescence detector directed at the same region of said plasma stream, said fluorescence detector including means matched to the characteristic radiation of said energizing illuminator, said energizing illuminators and said fluorescence detectors mounted in an offset radial array about said central axis; and
   (d) a readout system coupled to said plurality of optical stations and including a multiplexer and means for intermittent modulation of said energizing illuminators.

8. The fluorescence spectrometer of claim 7 wherein said energizing illuminator is a modified hollow cathode lamp characterized by a construction enabling the collection of a wide angle of radiation from its hollow cathode.

9. A fluorescence spectrometer for time division multiplexing multielement analysis of samples comprising:
   (a) a sample introduction system for dispersing a sample solution including means to introduce a reducing agent into said sample solution;
   (b) a plasma stream for atomizing said dispersed sample solution and directed along a central axis, said plasma stream controlled by an inductively coupled radio frequency generator coupling energy into said plasma stream sufficient to cause said dispersed sample solution to populate the ground state of energy level of said sample;
   (c) a plurality of modules radially surrounding said central axis for irradiating said atomized sample and for detecting the consequent fluorescent emission from said irradiated atomized sample in said plasma stream, with each of said plurality of modules being replaceable and angularly adjustable relative said central axis; and
   (d) a readout system coupled to said plurality of modules and including a multiplexer and means for intermittently modulating said plurality of modules.

10. The fluorescence spectrometer of claim 9 wherein each of said plurality of modules includes an energizing illuminator and a superimposed and offset fluorescence detector disposed in a radial plane, said fluorescence detector including means matched to the the characteristic radiation of said energizing illuminator, said energizing illuminator and said fluorescence detector directed at the same region of said plasma stream.

11. The fluorescence spectrometer of claim 10 wherein said energizing illuminator is a modified hollow cathode lamp characterized by a construction enabling the collection of a wide angle of radiation from its hollow cathode.

* * * * *